United States Patent
Lipman

(10) Patent No.: US 6,710,100 B1
(45) Date of Patent: Mar. 23, 2004

(54) FLUID ABSORBING, ADHESIVE HYDROCOLLOID COMPOSITIONS

(75) Inventor: Roger David Arnold Lipman, Turnhout Bus 2 (BE)

(73) Assignee: Avery Dennison Corporation, Pasadena, CA (US)

( * ) Notice: Subject to any disclaimer, the term of this patent is extended or adjusted under 35 U.S.C. 154(b) by 12 days.

(21) Appl. No.: 10/110,463

(22) PCT Filed: Oct. 13, 2000

(86) PCT No.: PCT/GB00/03931

§ 371 (c)(1),
(2), (4) Date: Aug. 22, 2002

(87) PCT Pub. No.: WO01/30406

PCT Pub. Date: May 3, 2001

(51) Int. Cl.$^7$ .......................... C08L 15/00; C08L 89/00
(52) U.S. Cl. ............................. 523/111; 524/22; 524/45; 524/54; 524/55; 524/474; 428/497; 428/532
(58) Field of Search .......................... 523/111; 524/22, 524/45, 54, 55, 474; 428/497, 532

(56) References Cited

U.S. PATENT DOCUMENTS

| | | |
|---|---|---|
| 3,339,546 A | 9/1967 | Chen |
| 3,972,328 A | 8/1976 | Chen |
| 4,231,369 A | 11/1980 | Sorensen et al. |
| 4,427,737 A | 1/1984 | Cilento et al. |
| 4,477,325 A | 10/1984 | Osburn |
| 4,551,490 A | 11/1985 | Doyle et al. |
| 4,647,613 A | 3/1987 | Jadamus et al. |
| 4,738,257 A | 4/1988 | Meyer et al. |
| 5,674,242 A * | 10/1997 | Phan et al. .................. 606/198 |
| 5,859,114 A | 1/1999 | Davis et al. |

FOREIGN PATENT DOCUMENTS

| | | |
|---|---|---|
| DE | 36 18 941 A | 12/1987 |
| DE | 36 18 941 A1 | 12/1987 |
| GB | 1 576 522 | 10/1980 |
| GB | 1576522 | 10/1980 |
| JP | 1170678 A | 7/1989 |
| JP | 2142878 A | 5/1990 |
| WO | WO 99/11728 | 3/1999 |
| WO | WO 99/14282 | 3/1999 |
| WO | WO 00/27014 | 6/1999 |

OTHER PUBLICATIONS

International Search Report of PCT/GB00/03931, dated Mar. 9, 2001.
International Preliminary Examination Report of PCT/GB00/03931, dated Jul. 24, 2001.

* cited by examiner

Primary Examiner—Kriellion A. Sanders
(74) Attorney, Agent, or Firm—Christie, Parker & Hale, LLP

(57) ABSTRACT

A fluid-absorbing, composite material that is pressure sensitive adhesive and which is made of a mixture comprising a continuous phase formed from a pressure sensitive adhesive matrix, and a discontinuous phase substantially comprised of one or more natural or synthetically derived water soluble and/or water insoluble absorbents, characterised in that the continuous phase contains trans-polyoctenamer polymer, which material serves to elevate the shear strength of the composite. Because of its low melting point, compositions containing trans-polyoctenamer polymer are very easy to process. Formulations can be prepared that have only weakly adhesive properties, also formulations that are suitable as primary dressings for various hard-to-heal and chronic wounds. The pressure sensitive adhesive can also be combined with a non-adhesive, water impervious film, or other backing material, and can be used as the protective adhesive skin barrier component of ostomy pouches.

14 Claims, No Drawings

FLUID ABSORBING, ADHESIVE HYDROCOLLOID COMPOSITIONS

CROSS-REFERENCE TO RELATED APPLICATION

This application claims priority of International application number PCT/GB00/03931, filed Oct. 13, 2000, which in turn claims priority of British application number 9924374.3, filed Oct. 14, 1999, and British application number 9924375.0, filed Oct. 14, 1999.

This invention relates to a fluid-absorbing, composite material that is pressure-sensitive and comprises a continuous phase formed from a pressure-sensitive adhesive matrix and a discontinuous phase substantially comprised of one or more natural or synthetically derived water soluble and/or water insoluble absorbents.

Pressure sensitive adhesive materials are used in many medical device fields and are made into products such as tapes, bandages, surgical drapes, IV dressings and the like. Hydrocolloid pressure sensitive adhesives are medically useful adhesives that have been known for about 30 years and were originally developed as bandages for the oral cavity to aid in delivery of drugs to the gingiva. Hydrocolloid adhesives have been hitherto unique in that they are inherently adhesive and inherently absorbent. They are useful as wound dressings because they can be applied directly to open wounds and secured on the surrounding intact skin, and as skin barriers because they protect the peristomal skin of ostomy patients. Many hydrocolloid skin barriers are known and are used for these purposes. The more modern of these adhesives are "integrated". In this context, "integrated" means those compositions that substantially retain their dimensional stability and form when saturated with wound exudate and/or other body fluid. "Non-integrated" means those compositions which become soft gels and amorphous as they become saturated with fluid. The shear strength of both integrated and non-integrated compositions can be improved using the teachings of the present invention, and the integrity of non-integrated compositions will also generally be increased.

The first hydrocolloid compositions to be described were non-integrated. U.S. Pat. No. 3,339,546 discloses compositions which are inelastic, and which are non-integrated, i.e. which do not maintain their dimensional stability and become amorphous when imbibed with wound fluid or other body fluid. A typical formulation taught by this prior art is the composition formed from low molecular weight polyisobutylene (40% by wt), pectin (20% by wt), sodium carboxymethyl cellulose (20% by wt) and gelatin (20% by wt). This formulation was used as a dressing for the gingiva but is also believed to be the basis of commercially successful skin barrier and wound care products. Such compositions form a soft gel when in contact with an exuding wound, and the resultant gel remains in the wound when the dressing is removed. This lack of integrity is a drawback. The gel must be removed from the wound at the time the dressing is changed. This is usually done by irrigation, which is time consuming for the nurse and painful for the patient. Adhesives taught by this patent also normally have relatively low shear strength, which can be a drawback in some use situations, particularly those in ostomy care, where the adhesive must retain on the abdomen a pouch containing body waste.

The lack of integrity was a serious drawback in the use of these dressings and barriers and much development was completed in efforts to overcome the deficiency. Thus, British Patent 1,576,522 corresponding to U.S. Pat. No. 4,231,369, describes improved hydrocolloid compositions that are integrated. There is provided a sealing material for ostomy use consisting of a hydrocolloid dispersed in a continuous phase of styrene-isoprene-styrene copolymer, or other thermoplastic elastomer such as an ethylene-propylene copolymer. Also present is a hydrocarbon tackifier and optionally an oil extender and an antioxidant. This material is said to have the advantage of being elastomeric and flexible. However, the absorption rate is lower than hydrocolloids made in accord with U.S. Pat. No. 3,339,546.

The shortcomings of barriers and dressings based upon formulae such as are described in U.S. Pat. No. 3,339,546 are also recognised by both U.S. Pat. No. 4,477,325 and U.S. Pat. No. 4,738,257. These two later patents disclose barriers and dressings based on an integrated formulation containing a continuous phase composed of a blend of high vinyl acetate EVA copolymer (51% wt VA and 49% wt ethylene) and low molecular weight polyisobutylene, in which is dispersed a discontinuous phase containing a blend of a superabsorbent material, pectin and sodium carboxymethyl cellulose. The function of the EVA copolymer is to cross link in the presence of ionising radiation, such as gamma radiation at a dosage of, for example, 25 KGy, which would be used to sterilise dressings formed from the compositions of the invention. The cross-linked network is formed essentially from the EVA polymer by irradiation of the EVA containing elastomeric phase. If the composition is to be used as an ostomy barrier, the gamma radiation is an expensive process to achieve integration, because ostomy products are not normally sold sterile. If the adhesive composition is used non-sterile, its shear strength is low.

U.S. Pat. No. 4,551,490 describes integrated hydrocolloid adhesives modified by diluting the amount of styrene-isoprene-styrene block copolymer present in the composition. The patent provides a medical grade pressure sensitive adhesive composition comprising a heterogeneous mixture of one or more polyisobutylenes or blends of polyisobutylenes and butyl rubber, one or more styrene radial or block copolymers, a tackifier, mineral oil and one or more water soluble and/or swellable hydrocolloid gums. It is believed that the polyisobutylenes, butyl rubber, mineral oil and tackifier serve to modify and plasticise predominantly the isoprene segment of the block/radial copolymer. In particular, the mineral oil is said to provide increased extensibility and aggressiveness of the adhesive. It is believed that the teachings of this patent form the basis of the commercially available hydrocolloid dressing products DuoDerm and Signa Dress. However, it has been found that the rates of absorption of saline with these compositions is very slow, and not very reproducible, and moreover very much less than the absorption levels available with the compositions of U.S. Pat. No. 3,339,546.

Our co-pending Application WO99/14282 describes a pressure sensitive adhesive material made of a weakly elastic mixture comprising a continuous phase formed from a blend of a physically cross-linked solid rubbers such as a styrene-isoprene-styrene triblock copolymer with a styrene-isoprene diblock copolymer, a compatible tackifying resin and a low molecular weight polyisobutylene, optionally modified by inclusion within the continuous phase of a quantity of butyl rubber, and a discontinuous phase comprising one or more hydrocolloids that are soluble and/or swellable in water. Small quantities of additives such as stabilisers and fumed silica may be present. The adhesive layer can be combined with a non-adhesive, water impervious film and can be used in wound care, ostomy care and in other medical products.

Our co-pending Application WO99/11728 describes a pressure sensitive adhesive material made of an elastic mixture comprising a continuous phase formed from a physically cross-linked solid rubber such as a styrene-isoprene-styrene block copolymer, and a compatible liquid rubber, such as a liquid styrene-isoprene rubber, and a discontinuous phase comprised of one or more absorbents that are swellable or soluble in water. Resinous materials are preferably absent, but additives such as polybutenes, polyisobutylene, mineral oil, stabilisers, and other rubbers, may be present. The pressure sensitive adhesives have the advantage over the prior art that they are extremely well integrated and contain no materials known to irritate skin and mucous membranes.

The composition of the present invention is characterised in that it contains 0.1 to 50% by weight, based on the continuous phase of trans-polyoctenamer.

The present invention provides compositions containing trans-polyoctenamer polymer that overcome some of the problems associated with the prior art. The present hydrocolloid adhesives have different and sometimes unique properties as compared to known hydrocolloid adhesives. Compositions may be formulated within the scope of the invention that have no leachable components that would contaminate a healing wound, and they can be used in wound care, ostomy care and other medical products. Within the scope of the invention, formulations can be prepared that have only weakly adhesive properties, also formulations that are suitable as primary dressings for various hard-to-heal and chronic wounds. By judicious choice of ingredients within the scope of the invention, compositions can be formulated that are relatively clear or translucent, and so are able to allow a visual assessment of the healing progress and the condition of a wound under a dressing.

One aspect of the present invention relates to barriers and wound dressings comprising a layer of absorbent adhesive coated on a non-adhesive, waterproof film. This construction is useful in a number of ways. One of these is for bandaging purposes, especially on movable body parts such as joints or on curved surfaces of the body. Wounds such as blisters, burns, venostasis ulcers and decubitus ulcers may advantageously be treated with the products of the invention. Another important use is for the protection of the skin around body openings, especially around the surgically created openings known as colostomies, ileostomies and urostomies.

Another aspect of the invention comprises fluid absorbable pressure sensitive adhesives that contain an antimicrobial agent such as silver sulfadiazine, quaternary ammonium compounds, povidone-iodine, and the like. Such agents may be advantageously incorporated into the formulations of the instant invention to yield absorbent adhesives that can be made into dressings or pads for infected or colonised wounds.

A further aspect of the present invention comprises fluid absorbable pressure sensitive adhesives that are only weakly adhesive, and that may lose most of this low level of adhesion as the formulation absorbs for example wound exudate. Such materials, formulated within the scope of the invention, are especially useful as pads for adhesive bandages and dressings, adhesive pads, surgical pads and the like. In this embodiment, the materials would generally be held in place on the body by other pressure sensitive adhesives, and would function as an island, or central pad attached to one side, the wound contacting side, of a carrier or backing or fabric. In this embodiment, formulations are envisaged that optionally may contain an effective amount of an antimicrobial or antibiotic substance.

Still another aspect of the present invention relates to integrated absorbent pressure sensitive adhesives that are processable at lower temperatures than prior art materials. The rubbery trans-polyoctenamer polymer may be incorporated into the formulations of the instant invention at relatively low temperatures, say at 80–90° C. The thermoplastic elastomers of prior art integrated formulations must be processed at temperatures of at least 160° C., and preferably under a nitrogen atmosphere, in order to melt the thermoplastic elastomer and plasticise it effectively. The trans-polyoctenamer polymer melts at much lower temperatures. At these lower processing temperature, fewer unwanted side reactions or thermal and oxidative degradation occurs and lower quantities of processing stabilisers can be used. This in turn minimises the amounts of potential trace irritants and allergens in the finished adhesive. Within the scope of the invention, the trans-polyoctenamer may be advantageously incorporated with or without the concomitant inclusion of other thermoplastic elastomers. The novel compositions gain improved shear strength in either case, and improved processability in the case where there is no accompanying additional thermoplastic elastomer in the formulation.

A fluid absorbing composition according to the invention comprises a continuous phase consisting of a mixture of a permanently tacky pressure sensitive adhesive and trans-polyoctenamer polymer and dispersed within the continuous phase a discontinuous phase of one or more water soluble and/or water swellable absorbent polymers.

The permanently tacky pressure sensitive adhesive component must be tacky at room temperature as well as at the skin temperature of patients. Also, the adhesive must be dermatologically acceptable, which means that after continuous contact with skin there is little adhesive residue upon removal and there is no significant reaction with the skin during the adhesion period. The adhesive strength of the continuous phase must be sufficient to adhere to the skin of the patient for the time determined by the use of the medical device of which the adhesive forms part. Suitable permanently tacky pressure sensitive adhesive components may be used singly or in admixture, and include natural rubber, polyisobutylene, styrene-diene block copolymers, styrene-hydrogenated diene block copolymers, butyl rubber, acrylic polymers, silicone rubber, polyurethane rubber, polyvinyl ether and other like substances.

Other ingredients such as tackifiers, plasticisers, and polymer stabilisers may be added to the continuous phase, to modify tack and optimise adhesion properties and to protect polymers from degradation during processing.

Trans-polyoctenamer is a crystalline metathesis polymer of cyclooctene with predominantly trans-isomeric double bonds. It is said to contain a mixture of linear polymer and macrocyclic groups within each polymer chain. The trans-polyoctenamer is exemplified by the materials Vestenamer 6213 and 8012, which are available from Hüls AG. The polymer as available from Hüls AG is said to contain 15% by weight of cyclic oligomers and 85% of acyclic polymer. The crystallinity of the polymer is thermally reversible and reforms very rapidly on cooling the polymer below its melting point. While the inventor does not wish to be bound by any particular theory of action, it is believed that the high ring content in the polymer chains serves to aid compatibility between otherwise incompatible elastomers. Also, the polymer crystallinity and the high ring content increases the amount of network formation within the permanently tacky pressure sensitive adhesive continous phase. Further, the low content of double bonds in the polymer improves the thermal and oxidative stability of the formulation, while the low viscosity of molten trans-polyoctenamer aids the processing of these materials. The trans-polyoctenamer is present in an amount corresponding to from 0.1% to 50% by weight of the continuous phase, preferably from 3% to about 25% by weight of the continuous phase.

The discontinuous phase comprises one or more hydrophilic polymers that are soluble or insoluble but swellable in water as the moisture-absorbing component. One or more swellable polymers may be present. Suitable insoluble swellable polymers include cross-linked sodium carboxymethyl cellulose, crystalline sodium carboxymethyl cellulose, cross-linked dextran and starch-acrylonitrile graft copolymer. The swellable polymer may also be a so-called "super absorbent" material such as starch sodium polyacrylate. Other hydratable polymers such as gluten and polymers of methyl vinyl ether and maleic acid and derivatives thereof may also be included in the discontinuous phase. Suitable water soluble polymers include sodium carboxymethyl cellulose, pectin, gelatine, guar gum, locust bean gum, collagen, karaya gum and the like. The discontinuous phase should not normally exceed 70% of the total weight of the adhesive, and preferably does not exceed 60% by weight of the adhesive, and may be comprised of any combination of soluble and/or insoluble absorbents.

Optional fillers such as silica and pigments and optional active ingredients such as epidermal growth factors and antimicrobial compounds may also be incorporated into the compositions of the invention. Silver sulfadiazine and benzalkonium chloride represent non-limiting examples of such antimicrobial ingredients. Also essential oils such as, for example, lavender oil or tea tree oil may be added in amounts sufficient for efficacy. Other active ingredients such as those that provide a warming or cooling sensation to the skin, for example capsaicin or menthol, may be added. Optional skin moisturising ingredients such as urea and polyols may be incorporated into the formulations of the instant invention.

The adhesive compositions of the invention may be conveniently prepared as follows. The components of the continous phase such as polyisobutylene, solid rubber, for example a styrene-olefin-styrene copolymer and any liquid ingredients such as a liquid rubber or a plasticiser are blended together in a suitable mixer, normally a sigma blade or Z-blade mixer with an extruder discharge. If thermoplastic elastomers are used, the mixer will need to be heated to about 170° C. A nitrogen flow of about 60 ml/sec through the mixer reduces the possibility of oxidative degradation of the rubber during processing. About 1 phr of a suitable stabiliser can be added at this stage. After blending of the rubbers, tackifiers, plasticisers etc. the mixer is usually cooled to 90–105° C. and the powdery ingredients are charged to the mixer together with the other optional ingredients, if present, and blended in for a period of time, usually 20–30 min. If high molecular weight rubbers are used, they may need to be premasticated in the mixer, or premilled on a rubber mill. The fully mixed mass is then removed from the mixer and then extruded or pressed to the desired thickness, and then laminated to suitable substrates.

The trans-polyoctenamer may be added to the contents of the mixer at the prepolymer stage, or later at the time the components of the discontinuous phase are added. Since the trans-polyoctenamer melts at low temperatures, it is very easily incorporated into the formulations.

Other processing techniques such as coating of the adhesive formulations from a solvent slurry, may also be employed, especially if the desired coating weight is less than about 0.25 mm (250 $\mu$m). A general procedure for this type of processing is given in U.S. Pat. No. 3,972,328, column 2, ll. 44–60, and also in U.S. Pat. No. 4,427,737, column 2, ll. 24–47. Specific process procedures are given for each of the examples below.

Test Methods

The formulations prepared in the examples were evaluated using a number of different test methods. Descriptions of these test methods follow.

Reverse Tack

Reverse tack of hydrocolloid adhesives is the maximum force necessary to remove a standard polyester strip brought into contact with the hydrocolloid without external force, from this hydrocolloid surface.

Procedure

Make the test panel self adhesive using double coated tape. Laminate the hydrocolloid adhesive on the test panel. Place the test panel with hydrocolloid in the lower clamp. Program the tensile tester. Place a polyester test strip of thickness 125 $\mu$m (5 mils) and dimensions (21 cm×2.54 cm) in the upper clamp, making sure that the total length of polyester under the clamp (loop) is 15 cm. Remove the release liner from hydrocolloid and start the measurement.

The reverse tack is the maximum force to remove the polyester strip from the hydrocolloid surface.

90° Peel Adhesion of Hydrocolloid Adhesives on Stainless Steel

Peel adhesion on stainless steel (SS) is the average force to remove a hydrocolloid adhesive, laminated under specified conditions on a SS panel, from the SS panel at constant speed and at an angle of 90°.

Procedure

Clean the SS-panel with solvent. Cut a hydrocolloid sample of 25.4 mm width and reinforce with reinforcing tape, laminate a paper strip at one end of the hydrocolloid sample using an overlap of about 1 cm. Remove the liner from the hydrocolloid sample and laminate the sample on the SS-panel with a 450 gm. roller at a speed of 150 cm/min. Allow the sample to dwell for 1 minute. Place the paper strip in the upper clamp and the SS-panel on the lower clamp, making sure that the angle between peel direction and SS-panel is 90°. Start the measurement using a crosshead speed of 300 mm/min. The angle must be kept 90° until the measurement is completed. The 90° peel adhesion is the average force to remove the hydrocolloid strip from the SS-panel.

Static Shear of Hydrocolloid Adhesives

Static shear is the time necessary to remove a hydrocolloid adhesive, laminated on a stainless steel panel under specified conditions, from the test panel under influence of a specified weight.

Procedure

Condition the hydrocolloid samples at 23±1° and 50±2% relative humidity for 24 hours. Clean the SS shear panel with solvent. Cut a hydrocolloid strip of 25.4 mm width and 50 mm length. Reinforce the hydrocolloid strip with reinforcing tape. Laminate the hydrocolloid strip on the test panel using an overlap surface of 1 inch². Protect the free hydrocolloid with release liner. Put a weight of 500 g on the laminate for 1 hour. Reinforce the free hydrocolloid adhesive zone with reinforcing plastic and perforate. Place the test panel with hydrocolloid on the shear bar using a shear weight of 500 g. Re-zero the registration-clock. Note the time on the clock when the measurement is completed.

Static Absorption of Hydrocolloids

To determine the amount of fluid uptake into a known surface of hydrocolloid adhesive.

Procedure

Laminate the double coated tape with release liner on the upper side of the cup (contact zone for hydrocolloid). Fill the cup with 30 ml NaCl solution (0.9% wt). Cut a sample of hydrocolloid of about the same size as the outer cup diameter. Weigh the sample ($W_1$). Laminate the sample onto the cup, making sure that the seal between the hydrocolloid sample and the cup is water tight. Turn the cup upside down and put it in the oven at 37° C. for 24 hours. Cool down. Remove the hydrocolloid from the cup and weigh ($W_2$). Calculate the water fluid absorption (g/sqm.24 h) with the formula:

$$abs=(W_2-W_1)/0.002375$$

(surface contact zone salt solution/hydrocolloid=0.002375 sq. m)

Determination of Cold Flow

The flow of the hydrocolloid under influence of a specified pressure and after a specified time, is measured.

Procedure

Condition the hydrocolloid samples at 23±1° C. and 50±2% relative humidity for 24 hours. Cut 5 samples of hydrocolloid using a 35 mm circular die-cutter Put a silicone paper on top of a first glass plate. Arrange the 5 samples on the silicone paper in a way that pressure is distributed equally. Measure the diameter of each sample with callipers, mark the exact place where the measurement is done. Put a plastic disk on each sample. Put another silicone paper and two glass plates over the construction followed by a weight of 10 kg. After 24 hours, measure the diameter of the samples where they are marked. Calculate the % increase of diameter of the samples. The cold flow is the % increase of diameter after 24 hours exposure to 10 kg (for 5 samples).

Determination of the Intearity

The integrity of a hydrocolloid is defined as its ability to resist breakdown by biological fluids. The test measures the weight percentage of hydrocolloid retained after exposure to saline under specified conditions.

Procedure

Condition the hydrocolloid samples at 23±1° C. and 50±2% relative humidity for 24 hours. Cut circular samples from the hydrocolloid sheet 2,54 cm diameter. Weigh and record the samples ($W_i$). Place each sample in a 120 ml (4 oz) bottles with screw caps (Vel Catalog Number 1198017) with 50 ml physiological saline (NaCl 0,9% wt in water), cap the bottles and agitate on a bottle shaker at 200 speed for a period of 18 hrs. Remove the samples and dry them in the circulating air oven at 50° C. and 50% relative humidity until dry. This usually takes about 24 hours. Reweigh the sample ($W_f$). The Integrity Value of the sample is calculated using the following equation:

$$\text{Integrity Value (\%)} = 100 \times \frac{(W_f)}{(W_i)}$$

Note: The test may be run with hydrocolloid with or without carrier. However, the result may be affected, and suitable control samples should always be included.

The invention will now be further described by reference to the following non-limiting examples.

EXAMPLE 1–2

Examples 1 and 2 are hydrocolloid adhesives that comprise polyisobutylene, Vistanex LMMH, available from Exxon Chemical Company, as the basis of the continuous phase. Three powdery ingredients comprise the discontinuous phase; Genupectin USP100, available from Hercules Chemical Company, Blanose sodium carboxymethyl cellulose 7H4XF available from Aqualon Division of Hercules Chemical, and Gelatine 225 Bloom strength, available from SKW Biosystems.

A laboratory Z-blade mixer was used to prepare the hydrocolloid composition of Example 1. The three powders were blended in the mixer at 80° C., and the polyisobutylene was added to the powders and blended for 20 minutes. Using the same procedure, another formulation was prepared, identical to that of Example 1, except that trans-polyoctenamer, Vestenamer 8012, was added at the end of the preparation, while the temperature was maintained at 80° C. These materials had the compositions set out in Table 1.

TABLE 1

| Amount in mix, gm | Example 1 | Example 2 |
|---|---|---|
| Polyisobutylene, Vistanex LMMH | 203 | 203 |
| Genupectin USP100 | 99 | 99 |
| NaCMC Blanose 7H4XF | 99 | 99 |
| Gelatine 225 Bloom Strength | 99 | 99 |
| Vestenamer 8012 | — | 20 |
| Total Weight, gm | 500 | 520 |

The shear strength of Examples 1 and 2 were measured with the results shown in Table 2.

TABLE 2

| | Example 1 | Example 2 |
|---|---|---|
| Shear Strength, min | 56 | 93 |

The data show that Vestenamer 8012, when incorporated in the hydrocolloid at 80° C. in the amount shown, increased the shear strength to nearly double that without the Vestenamer 8012. These examples also clearly demonstrate the ease of incorporating the trans-polyoctenamer. It can be easily mixed into the formulation at the end of the processing cycle.

EXAMPLES 3–5

These examples utilise, as a basis, a continuous phase of styrene-isoprene thermoplastic elastomer, Kraton KD-1161N, tackified with a mixture of Adtac LV-E and Escorez 2203 LC. The Kraton KD-1161N is a blend of linear styrene/isoprene/styrene triblock copolymer and linear styrene/isoprene diblock copolymer. Such a material is available from Shell Chemical Company and has a bound styrene content of about 15% and a diblock content of 17%. The mixture of tackifying resins used was Oa cyclopentadienyl resin, Escorez 2203LC, available from Exxon Chemical, and Adtac LV-E, a C5 synthetic hydrocarbon resin available from Hercules Chemical Company. The polyisobutylene, Vistanex LMMH, is available from Exxon Chemical Company. The Irganox 1010 is a hindered phenolic antioxidant manufactured by Ciba.

A hydrocolloid adhesive, Example 3, was prepared as follows. A sigma-blade mixer was purged with nitrogen gas and heated to 160° C. The speed of the front, faster, blade was 47 rpm. The Kraton KD-1161N and the Irganox 1010 were charged to the mixer at 160° C., and the mixer was started. After mixing for 5 minutes, the rubbery crumb coalesced, and the mixture of tackifying agents was added with continued mixing and nitrogen purging. After the tackifiers had completely mixed with the rubber, the mixer was cooled to 105° C. and the polyisobutylene was added. After mixing for 10 minutes, the mixer was further cooled to 90° C. and the powdered ingredients were added. The total time for this operation was about 90 minutes. The finished hydrocolloid was removed from the mixture with a spatula and pressed between two sheets of silicone release paper in a hydraulic press with the platens maintained at 90° C.

Examples 4 and 5 were made in a similar way, adding the Vestenamer 8012 as the last ingredient at the end of the process. The results are shown in Table 3.

TABLE 3

| Example No | 3 wt % | 4 wt % | 5 wt % |
|---|---|---|---|
| Vistanex LMMH | 28.0 | 28.0 | 28.0 |
| GenuPectin USP 100 | 14.0 | 14.0 | 14.0 |
| Blanose 7H4XF | 14.0 | 14.0 | 14.0 |
| Aqualon A500 | 14.0 | 14.0 | 14.0 |
| Vestenamer 8012 | — | 5.0 | 10.0 |
| Kraton D-1161NS | 11.3 | 9.4 | 7.53 |
| Adtac LV-E | 6.0 | 5.0 | 4.0 |
| Escorez 2203 LC | 12.5 | 10.4 | 8.33 |
| Irganox 1010 | 0.2 | 0.17 | 0.13 |
| Total | 100 | 100 | 100 |

The test results obtained on these formulations, compared to a commercially available hydrocolloid product from the 3M Company are set out in Table 4.

TABLE 4

| | Ex. 3 | Ex. 4 | Ex. 5 | 3M Hydrocolloid |
|---|---|---|---|---|
| Reverse tack N/in | 34.6 | 21.3 | 18.8 | 14.0 |
| Peel 90° S.S. N/in | 17.2 | 10.4 | 4.2 | 9.9 |
| Shear 0.5 kg, min | 239 | 502 | 920 | 141 |
| Thickness, mm | 0.90 | 0.99 | 1.2 | 0.43 |
| Static Absorption | 7175 | 6998 | 6594 | 2545 |

TABLE 4-continued

| | Ex. 3 | Ex. 4 | Ex. 5 | 3M Hydrocolloid |
|---|---|---|---|---|
| $gm/m^2/24hr$ Cold flow 23° C., % | 4.0 | 1.6 | 0.7 | 0.7 |

The data show clearly that the products of the invention show improved properties over the 3M material and over example 3. For instance, Examples 4 and 5 have progressively improved shear strength, which is important for use of these adhesives as barriers for ostomy pouches. Examples 4 and 5 also have excellent cold flow performance, important for gentle removal of dressings from the often compromised skin around stomas, and for ensuring no transfer to the skin of adhesive that may ooze out from the edge of the adhesive barrier. Note that the Examples 4 and 5 adhesives still possess higher tack than the product from 3M, and that the absorbent capacity of compositions 4 and 5 of the invention are not significant lower than that of Example 3, showing that trans-polyoctenamer polymer has no deleterious effect on absorption capacity.

EXAMPLES 6–11

In a similar fashion to the above, examples 6–11 were prepared, with the compositions shown in Table 5 below, and the products evaluated. In these examples, a lower molecular weight grade of trans-polyoctenamer polymer, Vestenamer 6312 available from Hüls AG, was used in the formulations. The Vector 4111 is a 100% triblock S-I-S elastomer available from Exxon Chemical, the Regalite 101 is a synthetic cycloaliphatic resin available from Hercules Chemical Company, the Irgafos 168 is an organophosphite stabiliser available from Ciba and the Irganox 565 is a hindered phenolic antioxidant available from Ciba.

TABLE 5

| Wt % | Ex 6 | Ex 7 | Ex 8 | Ex 9 | Ex 10 | Ex 11 |
|---|---|---|---|---|---|---|
| Vistanex LMMH | 26 | 26 | 26 | 26 | 26 | 26 |
| Pectin USP100 | 14 | 14 | 14 | 14 | 14 | 14 |
| Blanose 7H4XF | 14 | 14 | 14 | 14 | 14 | 14 |
| Aqualon A500 | 14 | 14 | 14 | 14 | 14 | 14 |
| Vestenamer 6312 | — | 5 | 10 | — | 5 | 10 |
| Kraton D-1161NS | 12.0 | 10.1 | 8.28 | — | — | — |
| Adtac LV-E | 6.4 | 5.4 | 4.4 | 5.78 | 4.88 | 3.98 |
| Escorez 2203 LC | 13.3 | 11.2 | 9.16 | — | — | — |
| Irganox 1010 | 0.21 | 0.18 | 0.14 | — | — | — |
| Vector 4111 | — | — | — | 11.5 | 9.73 | *7.93 |
| Regalite 101 | — | — | — | 14.4 | 12.1 | 9.92 |
| Irgafos 168 | — | — | — | 0.16 | 0.13 | 0.11 |
| Irganox 565 | — | — | — | 0.08 | 0.07 | 0.06 |
| Total, % | 100 | 100 | 100 | 100 | 100 | 100 |

The hydrocolloids were pressed to a uniform thickness of 0.82+/−0.06 mm in a platen press at 90° C. between two sheets of silicone coated release paper, and the samples were tested with the results shown in Table 6.

TABLE 6

|  | Ex 6 | Ex 7 | Ex 8 | Ex 9 | Ex 10 | Ex 11 |
|---|---|---|---|---|---|---|
| Sample Thickness, mm | 0.88 | 0.79 | 0.80 | 0.78 | 0.77 | 0.86 |
| Reverse Tack, N/25 mm | 28.8 | 24.3 | 19.7 | 34.9 | 24.6 | 18.4 |
| Peel Adhesion, N/25 mm | 9.8 | 9.7 | 6.9 | 15.4 | 9.6 | 6.8 |
| Shear Strength, min | 255 | 339 | 456 | 327 | 461 | 576 |
| Cold Flow, % increase/24 hr | 4.3 | 1.5 | 0.8 | 2.7 | 1.4 | — |
| Static Absorp, g/sq.m/24 hr | 6598 | 6589 | 6055 | 6918 | 7133 | 7090 |
| Integrity, % | 60 | 77 | 61 | 61 | 66 | 73 |

The influence of the trans-polyoctenamer is very clearly seen in these examples. With increasing trans-polyoctenamer, 0, 5 and 10 wt %, the tack decreases slightly but uniformly, the peel adhesion decreases, the shear strength increases dramatically, the cold flow is greatly improved, the absorption level is unaffected and the integrity increases marginally.

The data also show the effect on shear strength of a mixed di- and tri-block styrene-isoprene elastomer. Examples 6–8 have a mixed di- and tri-block elastomer, while examples 9–11 are integrated with a 100% tri-block Exxon Vector 4111 material, and the improved shear strength due to the 100% tri-block elastomer is clearly seen and is entirely in accord with expectation. But what is significant and unexpected is that the effect of the trans-polyoctenamer on shear strength is even more striking.

EXAMPLE 12–13

These examples utilise a continuous phase of styrene-isoprene thermoplastic elastomer, Kraton KD-1161N, plasticised with a styrene-isoprene liquid rubber, LVSI-101. The Kraton KD-1161N is a blend of linear styrene/isoprene/styrene triblock copolymer and linear styrene/isoprene diblock copolymer. This material is available from Shell Chemical Company and has a bound styrene content of about 15% and a diblock content of 17%. The LVSI-101 is a block copolymer of styrene and isoprene having a styrene content of about 13% and an isoprene content of about 87%, a glass transition of about −60° C., a melt viscosity of about 2400 poises at 50° C. and which is commercially available from Shell Chemical Company. The Irganox 1010 is a hindered phenolic antioxidant manufactured by Ciba.

A Z-blade mixer was purged with nitrogen gas and heated to 160° C. The speed of the front, faster blade was 30 rpm. Kraton KD-1161N (100 gm) and Irganox 1010 stabiliser (4.0 gm) were charged to the mixer at 160° C., and the mixer was started. After mixing for 5 minutes, the rubbery crumb coalesced, and 50 gm of liquid rubber styrene-isoprene copolymer, LVSI-101, was added with continued mixing and nitrogen purging. After a further ten minutes, the temperature was raised to 170° C. and the mixer front blade speed increased to 47 rpm. The LVSI-101 had at this point completely mixed with the rubber, and a further 50 gm of LVSI-101 was added. Ten minutes later, after blending of the second portion of the LVSI-101, a further 49 gm of LVSI-101 was added, and mixed for a further 10 minutes. In this way, approximately 50 gm portions of the charge of LVSI were added every 10 minutes until a total of 400 gm of LVSI-101 had been added. After a further 15 minutes, the intermediate adhesive, with the composition shown in Table 7, was dumped from the mixer. The total time for this operation was about 90 minutes.

TABLE 7

| Formula 2-18A | Gm. |
|---|---|
| LVSI-101 | 400 |
| Kraton KD-1161N | 100 |
| Irganox 1010 | 4 |

From this intermediate mixture, referred to as Formula No 2–18A in Table 8 below, in which all weights are in grams, a finished hydrocolloid was made having the following formula. The Aquasorb A500 is crystalline sodium carboxymethyl cellulose available from Aqualon, Division of Hercules Chemical. The Aerosil 200 is fumed silica available from Degussa AG.

TABLE 8

| Example No. | Vistanex LMMH | Aquasorb A500 | Formula 2-18A | Aerosil 200 |
|---|---|---|---|---|
| 12 | 65.6 | 98.5 | 164.1 | 6.7 |

The mixer temperature was reduced to 90° C. and the absorbent powder and silica was placed in the mixer and the mixer started. No nitrogen purge was used in this phase of the preparation. The Vistanex LMMH was added, the temperature raised to 105° C., the mix blended for 10 minutes, after which the intermediate adhesive, referred to as 2–18A in Table 8 above, was added. Blending was continued at 105° C. for a further 30 minutes, and the finished formulation was removed from the mixture with a spatula. The finished hydrocolloid was pressed between two sheets of silicone release paper in a hydraulic press with the platens maintained at 90° C.

In a similar manner to the above, except that the Vestenamer 8012 was incorporated into the Kraton KD-1161N prior to addition of the LVSI-101, an adhesive was prepared having the composition set out in Table 9.

TABLE 9

| Formula No: Amount gm. | 2-30A |
|---|---|
| LVSI-101 | 400 |
| Kraton KD-1161N | 100 |
| Vestenamer 8012 | 20 |
| Irganox 1010 | 4 |

From the above intermediate adhesive 2–30A, the following composition as shown in Table 10 was prepared as example 13. All weights in are grams:

TABLE 10

| Example No. | Vistanex LMMH | Aquasorb A500 | Formula 2-30A |
|---|---|---|---|
| 13 | 80 | 120 | 200 |

The formulated adhesive was extruded at 100° C. on to a silicone coated release paper, calendered down to a gauge of about 0.6 mm and laminated to an acrylic adhesive coated polyurethane film. The acrylic adhesive on the polyurethane film served as a tie coat to anchor the absorbent adhesive to the film. The results below in Table 11 show that the adhesive of Example 13 has twice the shear strength of that of Example 12.

TABLE 11

|  | Ex 12 | Ex 13 |
| --- | --- | --- |
| Reverse tack N/in | 12.3 | 23.2 |
| Peel 90° S.S. N/in | 5.0 | 10.2 |
| Shear 0.5 kg, min | 250 | 542 |
| Thickness, mm | 0.45 | 0.62 |
| Static Absorption gm/m²/24 hr | 2021 | 3793 |
| Cold flow 23° C., % | 1.0 | 1.6 |

EXAMPLES 14 and 15

These examples show the use of an acrylic polymer as the basis of the pressure sensitive adhesive matrix. In the preparation of each example the acrylic polymer, available from BASF as AC Resin A258, was added to the powdered absorbents in a Z-blade mixer at 90° C., and mixing continued until a homogeneous mixture was obtained. For example 15, trans-polyoctenamer, Vestenamer 6312, was added at the end of the preparation, while the temperature was maintained at 80° C. In each case, the resultant hydrocolloids were pressed at 90° C. between two sheets of silicone coated release paper in a hydraulic upstroking platen press to give sheets of material of about 0.8 mm in thickness. These materials had the compositions and properties shown below in Tables 12A and 12B.

TABLE 12A

| Amounts in gm: | Ex. 14 | Ex. 15 |
| --- | --- | --- |
| Acrylic AC Resin A258 | 290.2 | 180.0 |
| Blanose 7H4XF | 118.2 | 73.3 |
| Pectin USP100 | 118.2 | 73.3 |
| Aquasorb A500 | 118.2 | 73.3 |
| Vestenamer 6312 | — | 44.4 |
| Totals | 554.8 | 444.3 |

TABLE 12B

|  | Ex. 14 | Ex. 15 |
| --- | --- | --- |
| Integrity, % | 7 | 55 |
| Shear Strength, min | 56 | 155 |

The integrity and the shear strength of each adhesive were measured and the influence of the trans-polyoctenamer, Vestenamer 6312 was assessed in this way. It can be clearly seen that the trans-polyoctenamer increases both the integrity and the shear strength of the adhesive.

EXAMPLES 16–19

These examples show the incorporation of trans-polyoctenamer polymer in a hydrocolloid adhesive to produce low tack, low adhesion antimicrobial containing compositions, suitable for use as dressing pads for burns and other bacterially colonised wounds. In a similar fashion to the procedure described in Examples 12 and 13, an intermediate adhesive (No: 2–79A) was prepared as follows, with the composition shown in Table 13.

TABLE 13

| Material | gm | Wt % |
| --- | --- | --- |
| Kraton KD-1161N | 280.0 | 39.68 |
| Irganox 1010 | 5.6 | 0.79 |
| LVSI-101 | 420.0 | 59.52 |
| Total | 705.6 | 99.99 |

The Z-blade mixer was heated to 90° C. and the intermediate hot melt adhesive was added, and allowed to soften for 5 minutes. Then the Aquasorb was added at 100° C., with continuation of mixing for a further 15 minutes. After cooling to about 80° C., the antimicrobial additives were then added, followed by the Vestenamer 6213, and mixing was continued for 20 minutes, when the compounds were removed from the mixer and pressed at 90° C. between two sheets of silicone release paper. The tack and adhesion of these compositions is very low, and they are particularly suitable for application to wounds as dressing pads. The full compositions are set out in Table 14.

TABLE 14

| Material, gm | Ex 16 | Ex 17 | Ex 18 | Ex 19 |
| --- | --- | --- | --- | --- |
| LVSI Hot Melt 2-79A | 280 | 280 | 280 | 280 |
| Vestenamer 6213 | 120 | 120 | 120 | 120 |
| Aquasorb A500 | 120 | 120 | 120 | 120 |
| Tea Tree Oil | 0 | 0 | 10.6 | 0 |
| Benzalkonium chloride* | 0 | 0 | 0 | 1.56 |
| Silver sulfadiazine | 1.56 | 5.25 | 0 | 0 |
| Total | 521.56 | 525.25 | 530.60 | 521.56 |

*N-alkyl-N,N-dimethyl-N-benzylammoniumchloride, available from Lonza Specialty Chemicals

EXAMPLE 20

The adhesive compositions of the invention may include a skin moisturizing agent.

This example describes the preparation of a moisturising adhesive containing a high proportion, 40 wt %, of glycerine, and containing 20 wt % trans-polyoctenamer Vestenamer 6213 to give an adhesive whose adhesion power decreased with time of wearing.

An integrated hydrocolloid adhesive was prepared in a Z-blade mixer using LVSI-101, a liquid rubber component that is resin free, to tackify the solid S-I-S rubber component.

Description of the ingredients used follows. The LVSI-101 is a block copolymer of styrene and isoprene having a styrene content of about 13% and an isoprene content of about 87%, a glass transition of about −60° C., a melt viscosity of about 2400 poises at 50° C. and which is commercially available from Shell Chemical Company. The Kraton KD-1161NS is a blend of linear styrene/isoprene/styrene triblock copolymer and linear styrene/isoprene diblock copolymer available from Shell Chemical Company- It has a bound styrene content of about 15% and a diblock content of 17%. Irganox 1010 is a hindered phenol antioxidant manufactured by Ciba. The Aquasorb A500 is crystalline sodium carboxymethyl cellulose available from Aqualon, Division of Hercules Chemical Company.

The mixer was purged with nitrogen gas and heated to 160° C. The speed of the front, faster, blade was 30 rpm. The Kraton KD-1161NS and the Irganox 1010 were charged to the mixer at 160° C., and the mixer was started. After mixing for 5 minutes, the rubbery crumb coalesced, and 2.5 kg of the LVSI-101 was added with continued mixing and nitrogen purging. After a further ten minutes, the temperature was raised to 170° C. and the mixer front blade speed increased to 47 rpm. The LVSI had at this point completely mixed with the rubber, and a further 2.5 kg of LVSI was added. Ten minutes later, after blending of the second portion of the LVSI, a further 2.5 kg of LVSI was added, and mixed for a further 10 minutes. In this way, approximately 2.5 kg portions of the charge of LVSI were added every 10 minutes until all the 20 kg had been added. 15 minutes later, the intermediate adhesive was dumped from the mixer. The total time for this operation was about 90 minutes.

The mixer temperature was reduced to 90° C. and the absorbent Aquasorb A500 powder was added to the mixer. No nitrogen purge was used in this phase of the preparation. Blending was continued for a further 30 minutes, and the finished formulation was removed from the mixer. The intermediate hydrocolloid adhesive, 2–67A, had the composition set out in Table 15.

TABLE 15

| Amounts in kg | 2-67A | Wt % |
|---|---|---|
| LVSI-101 | 20.0 | 57.14 |
| Kraton KD-1161NS | 5.0 | 14.29 |
| Irganox 1010 | 0.2 | 0.57 |
| Aquasorb A500 | 9.8 | 28.00 |
| Total | 35.0 | 100.00 |

This intermediate hydrocolloid adhesive 2–67A was further compounded at 90° C. in a much smaller laboratory Z-blade mixer with glycerine, and trans-polyoctenamer Vestemer 6213 in the proportions shown in Table 16.

TABLE 16

|  | Wt % | Gms |
|---|---|---|
| 2-67A | 40 | 200.0 |
| Glycerine | 40 | 200.1 |
| Vestenamer 6213 | 20 | 100.0 |
| Total | 100 | 500.1 |

Thus, the finished composition had the following composition shown in Table 17.

TABLE 17

|  | Wt % |
|---|---|
| LVSI-101 | 22.86 |
| Kraton KD-1161NS | 5.71 |
| Irganox 1010 | 0.23 |
| Aquasorb A500 | 11.20 |
| Glycerine | 40.00 |
| Vestenamer 6213 | 20.00 |
| Total | 100.0 |

The formulated adhesive was pressed at 90° C. between two sheets of silicone coated release paper, and laminated to an acrylic adhesive coated non-woven fabric commercially available from Avery Dennison Specialty Tape Division, Turnhout, Belgium as MED1817. The acrylic adhesive on the non-woven fabric served as a tie coat to anchor the hydrocolloid adhesive to the non-woven fabric.

The composite adhesive laminate was cut into 2.5 cm×7.5 cm strips and was wear tested on the calves of four female panelists. The adhesive was initially moderately adhesive to skin. As the glycerine was absorbed into the skin, the composition became less tacky and less adhesive, causing the adhesive power to decrease with wearing time, and the adhesive to be only very weakly adhesive to the skin after about 8 hours of wear. After removal of the adhesive, the underlying skin was noticeably softer to the touch than the surrounding skin.

What is claimed is:

1. A pressure-sensitive adhesive composition comprising a continuous phase formed from a pressure-sensitive adhesive matrix and a discontinuous phase consisting essentially of one or more natural or synthetically derived water soluble and/or water-insoluble absorbents, characterised in that the composition contains 0.1 to 50% by weight, based on the continuous phase, of trans-polyoctenamer.

2. An adhesive composition according to claim 1 which is clear or translucent.

3. An adhesive composition according to claim 1 or claim 2 wherein the discontinuous phase constitutes not more that 70% by weight of the total composition.

4. An adhesive composition according to claim 3 wherein the discontinuous phase constitutes not more than 60% by weight of the total composition.

5. An adhesive composition according to claim 1 which also contains an antimicrobial agent.

6. An adhesive composition according to claim 1 wherein the trans-polyoctenamer constitutes from 3 to 25% by weight of the continuous phase.

7. An adhesive composition according to claim 1 wherein the discontinuous phase contains one or more swellable polymers.

8. An adhesive composition according to claim 7 wherein the discontinuous phase contains at least one swellable polymer selected from cross-linked sodium carboxymethyl cellulose, crystalline carboxymethyl cellulose, cross-linked dextran, starch-acrylonitrile graft copolymer and starch sodium polyacrylate.

9. An adhesive composition according to claim 1 wherein the discontinuous phase contains at least one hydratable polymer selected from gluten, polymers of methylvinyl ether and maleic acid and derivatives thereof.

10. An adhesive composition according to claim 1 wherein the discontinuous phase contains at least one water-soluble polymer selected from sodium carboxymethyl cellulose, pectin, gelatin, guar gum, locust bean gum, collagen and karaya gum.

11. An adhesive product comprising a layer of a pressure sensitive adhesive composition according to claim 1 coated on a backing or carrier material.

12. An adhesive product according to claim 11 wherein the backing material comprises a non-adhesive waterproof film.

13. An adhesive product according to claim 11 or claim 12 wherein the adhesive composition includes a skin-moisturizing agent.

14. A method of making an adhesive composition according to claim 1, wherein the trans-polyoctenamer is incorporated into the other components of the continuous phase at a temperature not exceeding 100° C.

* * * * *